United States Patent
Dong et al.

(10) Patent No.: US 8,048,385 B2
(45) Date of Patent: Nov. 1, 2011

(54) SENSING CHIP

(75) Inventors: Huang Yi Dong, Beijing (CN); Rao Yi, Beijing (CN); Liu Fang, Beijing (CN); Zhang Wei, Beijing (CN); Peng Jiang De, Beijing (CN); Dai Ohnishi, Kyoto (JP); Daisuke Niwa, Kyoto (JP); Atsushi Tazuke, Kyoto (JP); Yoshikatsu Miura, Kyoto (JP)

(73) Assignees: Rohm Co., Ltd., Kyoto (JP); Tsinghua University, Beijing (CN)

( * ) Notice: Subject to any disclaimer, the term of this patent is extended or adjusted under 35 U.S.C. 154(b) by 125 days.

(21) Appl. No.: 12/346,950

(22) Filed: Dec. 31, 2008

(65) Prior Publication Data
US 2009/0209028 A1    Aug. 20, 2009

(30) Foreign Application Priority Data
Jan. 4, 2008    (CN) .......................... 2008 1 0055626

(51) Int. Cl.
*G01N 21/75*    (2006.01)

(52) U.S. Cl. ...................................... 422/402

(58) Field of Classification Search ............ 422/57, 422/402
See application file for complete search history.

(56) References Cited

U.S. PATENT DOCUMENTS
| 7,671,996 | B2 | 3/2010 | Niwa et al. |
| 2006/0274314 | A1 | 12/2006 | Thompsen et al. |
| 2009/0066962 | A1 | 3/2009 | Niwa et al. |
| 2009/0209028 | A1 | 8/2009 | Dong et al. |

FOREIGN PATENT DOCUMENTS
| JP | 2003-042944 | 2/2003 |
| JP | 2003-279476 | 10/2003 |
| JP | 2006-250668 | 9/2006 |

OTHER PUBLICATIONS

K. Kuhira et al., "Theoretical understanding of an absorption-based surface plasmon resonance sensor based on Kretchmann's theory.", Anal. Chem. 74(3):696-701 (2002).
Shumaker-Parry J.S. et al., "Microspotting streptavidin and double-stranded DNA arrays on gold for high-throughput studies of protein-DNA interactions by surface plasmon resonance microscopy", Anal. Chem., 76(4):918-929 (2004).

*Primary Examiner* — Bobby Ramdhanie
(74) *Attorney, Agent, or Firm* — Fish & Richardson P.C.

(57) ABSTRACT

There is provided a sensing chip capable of measuring a refractive index by utilizing a long-range surface plasmon polariton, accurately measuring an accumulative refractive index in a wide range, and more easily enabling sealing for measurement. The present invention relates to the sensing chip which has a thin metal film or a strip-like metal grown on an underlayer, and has a dielectric that limits a refractive index and a dielectric buffer layer on an upper surface and a lower surface of the thin metal film or the strip-like metal. The dielectric buffer layer is attached onto the thin metal film or the strip-like metal. The thin metal film or the strip-like metal and the buffer layer are sandwiched between two dielectric layers. A hole is made in a surface of the upper dielectric layer to serve as a measurement groove.

6 Claims, 4 Drawing Sheets

A—A

B-B

C-C

SENSING CHIP

BACKGROUND OF THE INVENTION

1. Field of the Invention

The present invention relates to the photoelectron integration technical field, and more particularly, it relates to a sensing (measurement) chip for a refractive index of a long-range surface plasmon polariton applied in the region of photon integration, a sensor and the like.

2. Description of the Background Art

A surface plasmon polariton ((SPP), FIG. 1) is an electromagnetic field transmitted along the interface between a metal and a dielectric, and the amplitude thereof is exponentially attenuated in the dielectric in response to the distance from the interface. The SPP is a kind of surface wave whose electromagnetic field energy is concentrated in the vicinity of the interface between the metal and the dielectric, and hence the electromagnetic field on the metal surface is strong and extremely sensitive to the mode of the surface, particularly a change in the refractive index. Thus, the SPP is widely applied as a biochemical sensor.

As shown in FIG. 1, a conventional biochemical sensor of a surface plasmon polariton applies light 3 to a metal surface 1 easily forming surface plasma and changes the angle of incident light 3, so that the surface plasma is excited only by incident light of a certain specific angle 5. In this case, the power of reflected light 4 abruptly decreases. This specific angle is extremely sensitive to refraction of a substance 2 on a cross boundary of the metal surface, and the refractive index of substance 2 on the cross boundary of the metal surface can be measured by measuring angle 5 of the incident light when the power of the reflected light decreases. This conventional measuring method requires separate components such as a prism and a turntable, and is hence hard to adjust due to a large size. Further, the method is inferior in stability, and at a high cost. Therefore, universalization and application thereof are extremely limited.

When a metal portion is a thin film, two sets of surface plasmon polaritons are formed on an upper surface 101 and a lower surface 102 of the thin film, as shown in FIG. 2. When the thickness of the metal thin film decreases up to a constant degree, the two sets of surface plasmon polaritons are coupled with each other. The electric field distribution of such a coupled wave is mostly concentrated in an upper dielectric 2 and a lower dielectric 6 other than the metal and the coupled wave can be transmitted on the metal surface in a long-range manner with small transmission loss, and hence the same is referred to as long-range surface plasmon polariton (LR-SP). Such a long-range surface plasmon polariton is extremely sensitive to the difference between the refractive indices of upper dielectric 2 and lower dielectric 6 of the metal thin film, and the refractive index can be highly precisely measured when measuring loss of the long-range surface plasmon polariton or (and) a light spot size. However, although this method is highly precise, the measurement range is small, and the structure thereof is not suitable to sealing and practical use, but exerts disadvantageous influence on universalization and application.

As shown in FIG. 3, a chip measurement range can be adjusted by rendering a metal strip-like, adding a buffer layer 3 onto the metal while adding a reference arm 12 and another reference arm 13 to both sides of a measurement-waiting metal 11 and adjusting the thickness of the buffer layer, the chip can be sealed by conforming the same to the reference arms, and the strip-like metal is more suitable to direct excitation of an optical fiber. Transmission loss of such a long-range surface plasmon polariton is extremely sensitive to the difference between the refractive indices of an upper dielectric 7 and a lower dielectric 4 of the strip-like metal. Buffer layer 3 has a refractive indeed substantially identical to that of lower dielectric 4. Transmission loss caused by the difference between the refractive indices of lower dielectric 4 and a sample liquid can be reduced by comprising buffer layer 3. Therefore, an apparatus can sense an antigen-antibody reaction, SNPs, a gene-protein interaction, a cell/protein function, as well as a bio material and a biological reaction such as an associative function in high detection sensitivity. In addition, the buffer layer/metal structure is a structure effective for protecting the metal against damage from the liquid. Therefore, the apparatus can be used in a severer situation. In addition, this structure is suitable in relation to molecular modification. The buffer layer is so introduced that the measurement range and precision can be adjusted, and the refractive index of the liquid or an antigen-antibody reaction of an organism can be measured with high precision in a wide-ranging manner.

SUMMARY OF THE INVENTION

As shown in FIG. 4, the refractive index can be measured with high precision when measuring loss of the long-range surface plasmon polariton or (and) the light spot size. When the refractive index (abscissas in the drawing) of upper dielectric of the strip-like metal changes in a case where the refractive indices are fixed to 1.444 in buffer layer 3 and lower dielectric, loss (ordinates in the drawing) of the long-range surface plasmon polariton remarkably changes following this, and sensitivity decreases while the measurement range increases as the thickness of buffer layer 3 increases, as a measurement range 8 is shown in FIG. 4. Thus, the refractive index can be measured with high precision in a wide-ranging manner through the long-range surface plasmon polariton.

The present invention aims at providing an integratible sensing chip for a refractive index of a long-range surface plasmon polariton, in order to solve such problems in a conventional refractive measuring apparatus of a surface plasmon polariton that the apparatus is large-sized, requires a large number of components, is hard to adjust, and inferior in stability. The present invention simultaneously proposes a strip-like metal structure, a buffer layer structure and a reference arm structure, enlarges the measurement range of the sensing chip, and further puts the same into practice.

The sensing chip for a refractive index of a long-range surface plasmon polariton according to the present invention is a sensing chip having a metal thin film or a strip-like metal and having an upper limiting layer and a lower limiting layer made of silicon-rich silica $SiO_x$, $SiO_2$ or benzocyclobutene (BCB) formed on the upper and lower surfaces thereof as well as a dielectric buffer layer, and is characterized in that the dielectric buffer layer is made of silicon-rich silica $SiO_x$ or silicon nitride $SiN_y$ and attached onto a measurement groove of the metal thin film or the strip-like metal, the metal thin film or the strip-like metal and the buffer layer are sandwiched between $SiO_x$, $SiO_2$ or BCB constituting the upper limiting layer and the lower limiting layer, the upper layer surface of the said upper limiting layer made of $SiO_x$, $SiO_2$ or benzocyclobutene is perforated to form a measurement window (measurement groove) (where $0 \leq x \leq 2$ and $0 \leq y \leq 4/3$), all structures are grown on an Si underlayer, a GaAs underlayer, an InP underlayer or an $SiO_2$ underlayer, and the aforementioned chip forms a long-range surface plasmon polariton by a method of performing excitation on an end face of this metal thin film or the strip-like metal and measures a refractive index change of a liquid in the measurement groove or an antigen-antibody reaction of an organism from a change in transmission loss of this long-range surface plasmon polariton and/or a change in a light spot size.

The metal in the aforementioned metal thin film or the strip-like metal is any one of gold, silver, aluminum, copper, titanium, nickel and chromium, the thickness thereof is 1 nm to 100 nm, particularly preferably 10 nm to 100 nm, and the width of the strip-like metal is 50 nm to 100 μm, particularly preferably 2 μm to 20 μm.

The refractive index of the aforementioned dielectric is 1.0 to 4.0, particularly preferably 1.2 to 3.8, and the thickness of this dielectric is 1 to 10000 nm, particularly preferably 2 to 20 μm.

The aforementioned dielectric buffer layer is made of $SiO_x$ or $SiN_y$, the refractive index thereof is 1.0 to 4.0, particularly preferably 1.2 to 3.8, and the thickness of this dielectric is 1 nm to 10000 nm, particularly preferably 1 nm to 5 μm.

The thickness of the aforementioned $SiO_2$ is 1 μm to 20 μm.

The thickness of the aforementioned BCB is at least 1 μm.

The present invention measures the refractive index through the long-range surface plasmon polariton and introduces a strip-like structure, the buffer layer and a reference arm as profitable effects, whereby the has three advantages. First, the change in the transmission loss or (and) the change in the light spot size is employed as the target of measurement in place of a spatial reflected light angle of the prior art, whereby an integratible dielectric refractive index measuring apparatus can be provided. Second, buffer layer 3 has a refractive index substantially identical to that of lower dielectric 4. Transmission loss caused by the difference between the refractive indices of lower dielectric 4 and the sample liquid can be reduced by comprising buffer layer 3. Therefore, the apparatus can sense an antigen-antibody reaction, SNPs, a gene-protein interaction, a cell/protein function, as well as a bio material and a biological reaction such as an associative function in high detection sensitivity. In addition, the buffer layer/metal structure is a structure effective for protecting the metal against damage from the liquid. Therefore, the apparatus can be used in a severer situation. In addition, this structure is suitable in relation to molecular modification. The buffer layer is so introduced that the measurement range and precision can be adjusted, and the refractive index of the liquid or an antigen-antibody reaction of an organism can be measured with high precision in a wide-ranging manner. Third, convenience is aimed at coupling an optical fiber and a light guide end face, chip sealing is supported by the reference arm, the long-range surface plasmon polariton is excited by the method of coupling the optical fiber and the light guide end face, a control portion for spatial incident light is omitted, a pigtail fiber can be sealed in an attached chip, and this is an invention having a more practical industrial value.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The present invention provides an integratible sensing chip for a refractive index of a long-range surface plasmon polariton. The present invention simultaneously proposes a strip-like metal structure, a buffer layer structure and a reference arm structure, enlarges the measurement range of the sensing chip, and further puts the same into practice. The present invention is now described with reference to the drawings.

First, the structure is designed, and the material for and the thickness of a metal thin film, the width of a strip-like metal, the material for upper and lower limiting layers, the material for a buffer layer and the like are decided, so that a long-range surface plasmon polariton along the metal surface can be formed by end face excitation. On the basis of the results of the design, a strip-like pattern is formed by photolithography, the metal thin film of 10 nm to 100 nm in thickness is formed on the selected underlayer material by sputtering or vapor deposition, the strip-like metal is formed by lifting or wet etching, and the width of the strip-like metal is limited to 2 μm to 20 μm. Thereafter the buffer layer and the upper limiting layer are formed on the strip-like metal by a method such as sputtering, vapor deposition or spin coater hardening, and a measurement window is formed by wet or dry etching. Finally, a liquid is introduced into the measurement window (measurement groove) in response to direct necessity, or antibodies/antigens are incubated.

Example 1

Figure 1:
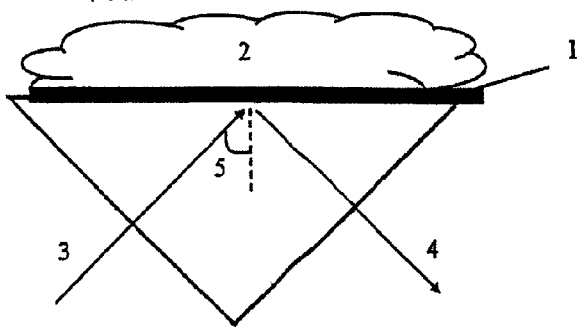
FIG. 1 is a diagram showing the principle of conventional measurement of a refractive index with a surface plasmon polariton, including a metal 1, a metal upper dielectric 2, incident light 3, reflected light 4 and an incident angle 5 therein.
Figure 2:
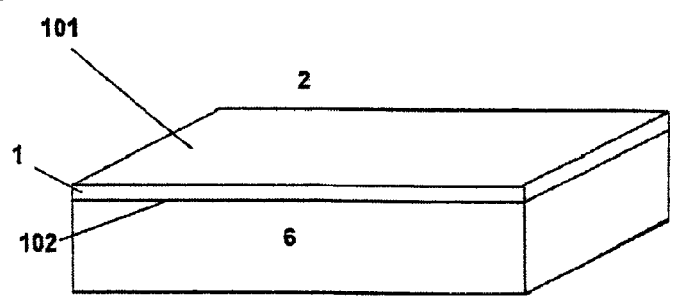
FIG. 2 is a diagram showing the structure of a metal thin film receiving a long-range surface plasmon polariton, having no reference arm and no buffer layer therein, and including a metal lower surface 101, a metal upper surface 102, a metal thin film lower dielectric 6 and a measurement-waiting dielectric 2 on the upper portion of the metal thin film.
Figure 3:
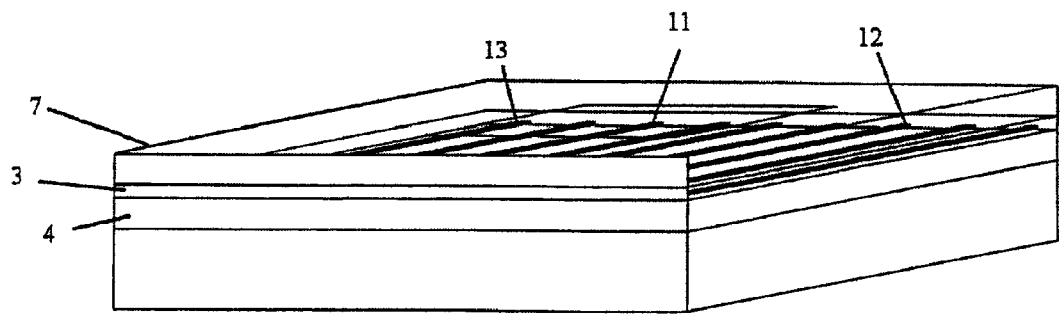
FIG. 3 is a diagram showing the structure of a strip-like metal receiving a long-range surface plasmon polariton, having reference arms and a buffer layer therein, and including a measurement arm 11, a first reference arm 12, a second reference arm 13, upper limiting dielectrics 7, a metal upper buffer layer 3 and a measurement-waiting dielectric 4.
Figure 4:
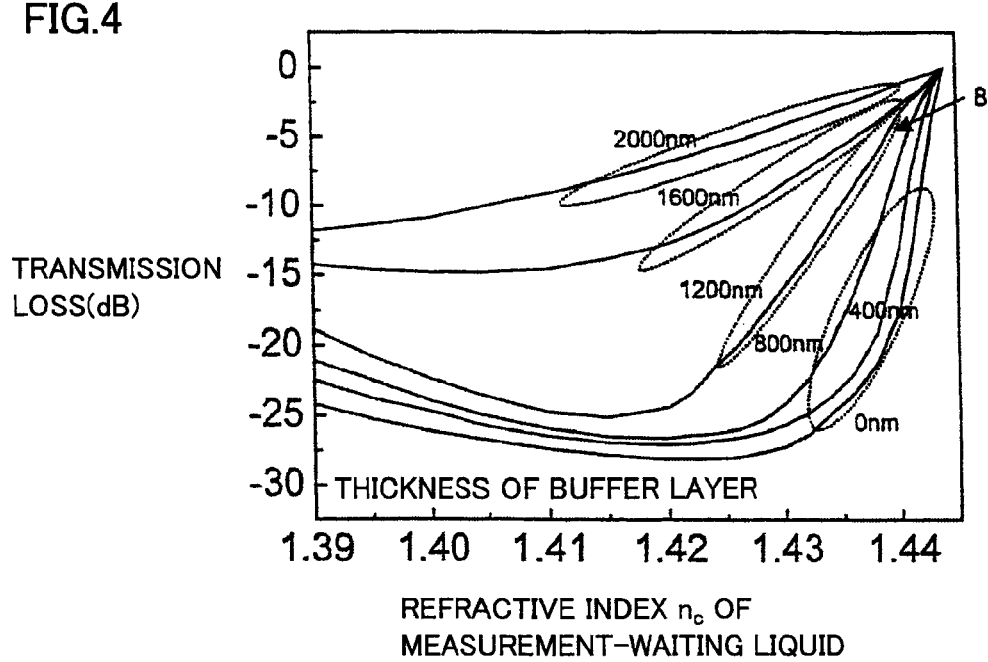
FIG. 4 is a diagram showing a change in transmission loss of a long-range surface plasmon polariton resulting from a refractive index of a measurement window, and 8 therein is a measurement zone.
Figure 5:
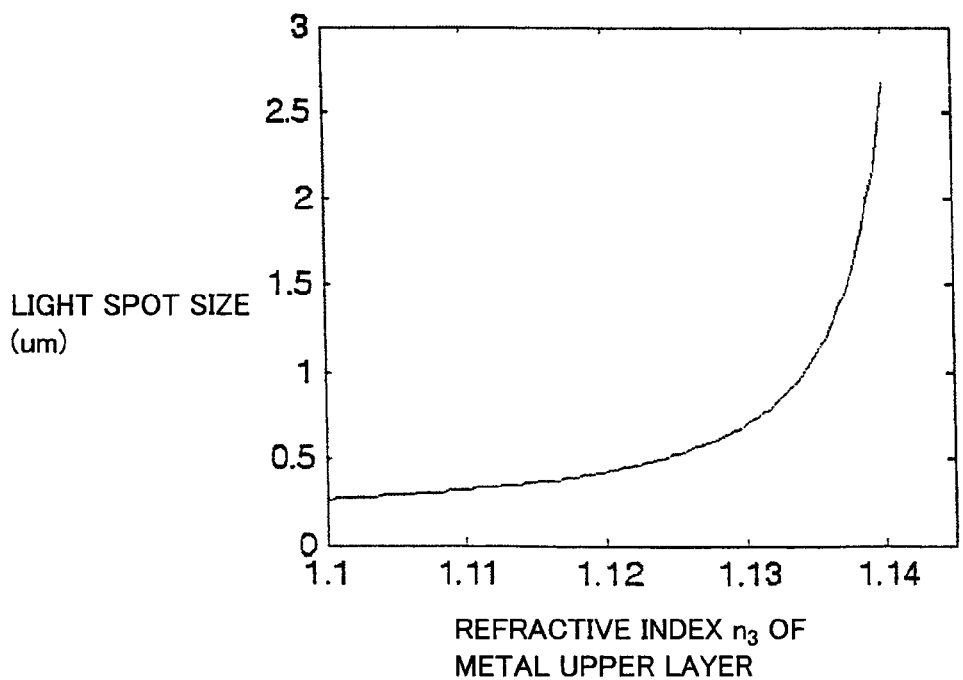
FIG. 5 is a diagram showing a change in a light spot size resulting from a change in a metal upper layer dielectric.
Figure 6:
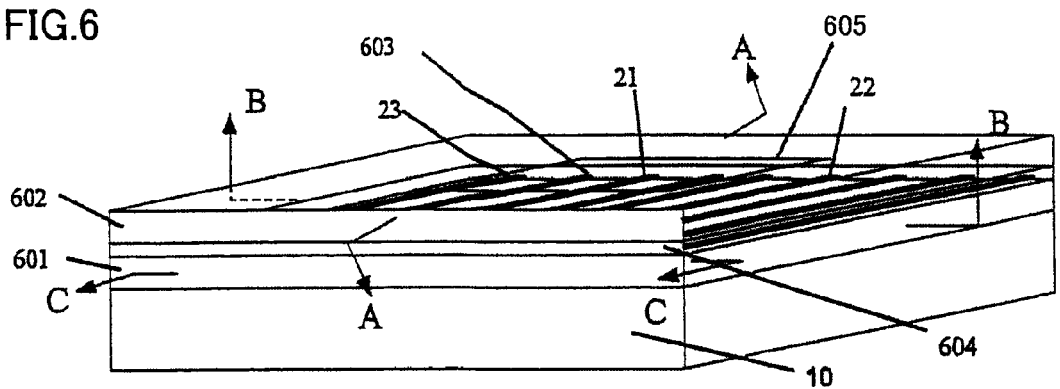
FIG. 6 is a diagram showing a sensing chip for a refractive index, of a long-range surface plasmon polariton including an $SiO_2$ lower limiting layer 601, an $SiO_2$ upper limiting layer 602, an Au thin film 603, a buffer layer 604, a measurement window 605, an Si substrate 10, a measurement Au arm 21, a first reference Au arm 22 an a second reference Au arm 23 therein.
Figure 7:
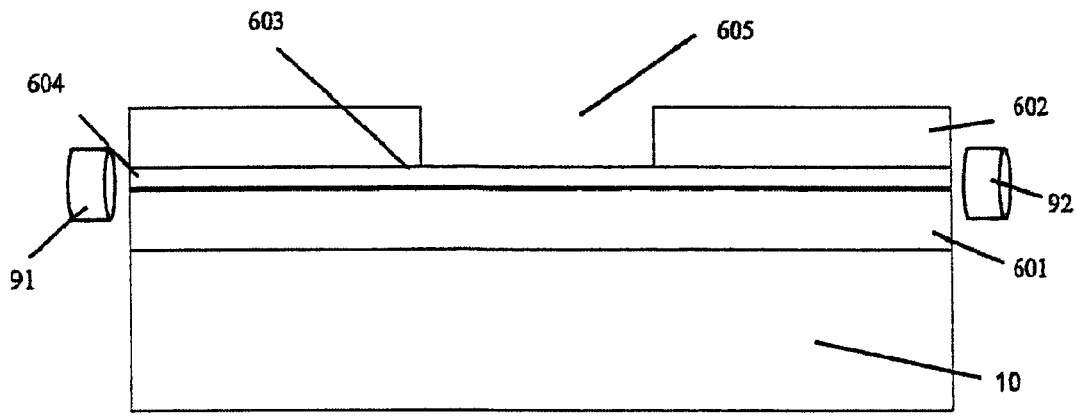
FIG. 7 is a diagram showing an A-A section in FIG. 6, including an incident optical fiber or light guide 91 for a surface plasmon polariton excited on an end face and an optical fiber or infrared sensing CCD 92 sensing a long-range surface plasmon polariton therein.
Figure 8:
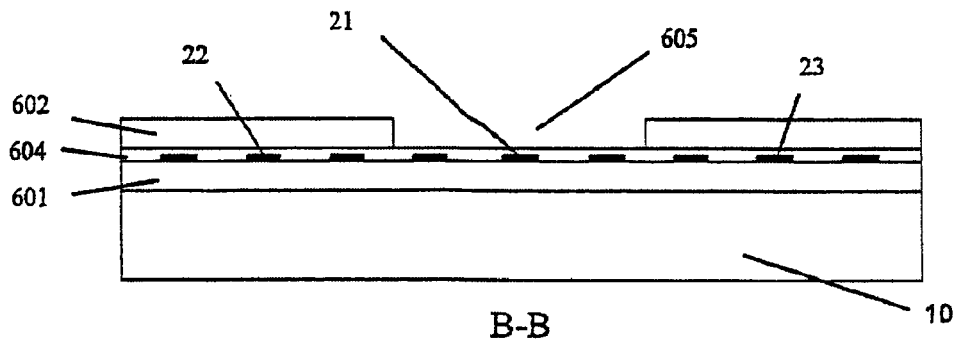
FIG. 8 is a diagram showing a B-B section in FIG. 6.
Figure 9:
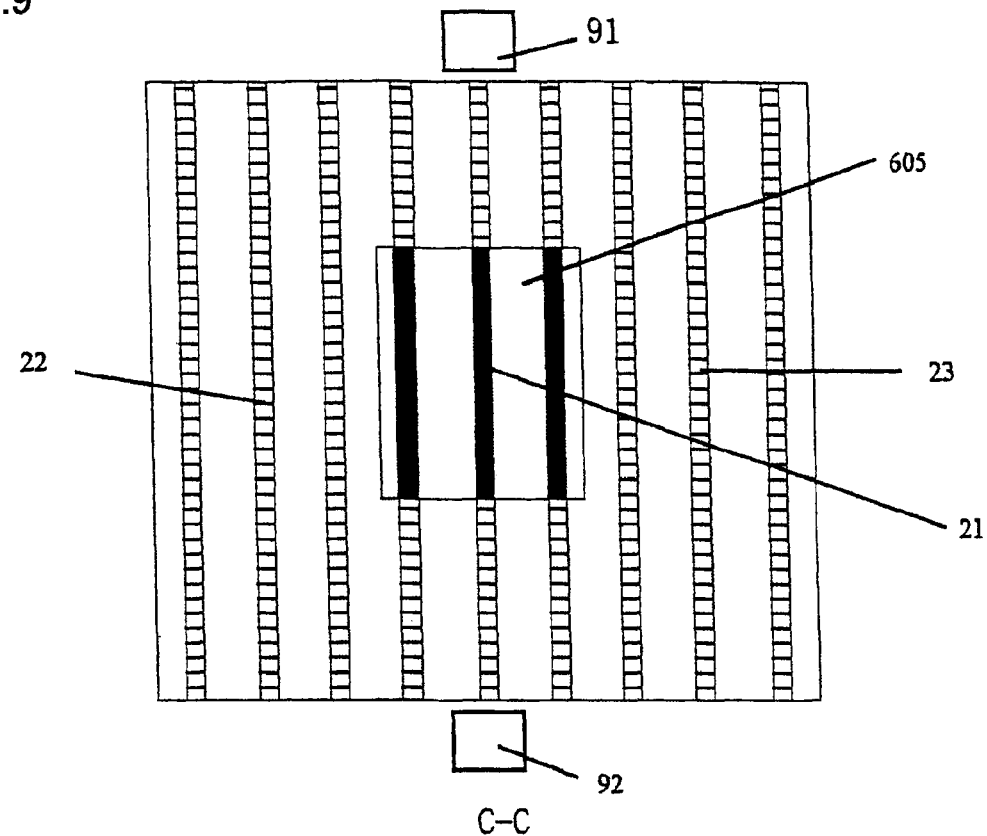
FIG. 9 is a diagram showing a C-C section in FIG. 6.

FIG. 6 is a diagram showing the basic structure of a sensing chip for a refractive index of a long-range surface plasmon polariton. FIG. 7 is an A-A sectional view of FIG. 6. FIG. 8 is a B-B sectional view of FIG. 6. FIG. 9 is a C-C sectional view of FIG. 6. An Si substrate (underlayer) 10 is selected. $SiO_2$ or $SiO_x$ is selected as the material for a lower limiting layer 601 and an upper limiting layer 602, and lower limiting layer 601 is formed on Si substrate 10 by PECVD. A strip-like pattern of 81m in width is formed on lower limiting layer 601 by photolithography. Then, an Au thin film 603 of 20 nm in thickness is formed by sputtering or vapor deposition, and a measurement Au arm 21, a first reference Au arm 22 and a second reference Au arm 23 are formed by lifting or wet etching. Thereafter a buffer layer 604 made of $SiO_x$ or $SiN_y$ is formed by a method such as sputtering, vapor deposition or spin coater hardening. In response to specific measurement conditions, the thickness of buffer layer 604 becomes 10 nm to 1 μm. Upper limiting layer 602 is formed by PECVD. Finally, a measurement window 605 of 2 mm in length and 200 μm in width is formed by wet or dry etching. The aforementioned chip is fixed, and an incident optical fiber 91 and a sensing optical fiber 92 are fixed to both sides thereof. The heights of incident optical fiber 91 and sensing optical fiber 92 must be conformed to the center of first reference Au arm 22, and the length of first reference Au arm 22 between incident optical fiber 91 and sensing optical fiber 92 is 3 mm. A light field emitted from incident optical fiber 91 excites surface plasmon polaritons on first reference Au arm 22. The thickness of the Au thin film is appropriate, whereby upper and lower surface plasmon polaritons are coupled to form a long-range surface plasmon polariton transmittable in a constant distance. The transmitted surface plasmon polariton is sensed by sensing optical fiber 92, the position of the optical fiber is adjusted, and the position in the vertical direction thereof is fixed while the horizontal position is adjusted up to measurement Au arm 21 when an output reaches the maximum. In this case, a measurement-waiting substance (transparent liquid whose refractive index is not larger than that of $SiO_2$) is introduced into measurement window 605. The refractive index of a dielectric in the measurement window entirely changes, whereby transmission loss of the long-range surface plasmon polariton can be sensitively changed unless a measurement range 8 shown in FIG. 4 is exceeded, the power of the surface plasmon polariton sensed by sensing optical fiber 92 changes by the change in the refractive index of the measurement-waiting substance, and hence the object of measuring the refractive index can be attained. The change in the refractive index of the dielectric may result from reaction between substances, and there are also a change in the overall refractive index of the substance resulting from a temperature, a pressure, an electromagnetic field, luminous intensity or the like and a change in the whole of the refractive indices of the substance components resulting from external environment.

The material for the Au thin film in this Example may be replaced with any one of silver, aluminum, copper, titanium, nickel and chromium or an alloy thereof, and the material for the Si substrate (underlayer) may be replaced with a material such as $SiO_2$, GaAs, InP, Cu or Al. This exerts no influence on the service function of this Example.

Example 2

FIGS. 6, 7, 8 and 9 are diagrams showing the basic structure of Example 2 of a sensing chip of a long-range surface plasmon polariton for a refractive index. An Si substrate 10 is selected. $SiO_2$ or $SiO_x$ ($0 \leq x \leq 2$) is selected as the material for a lower limiting layer 601 and an upper limiting layer 602, and lower limiting layer 601 is formed on Si substrate 10 by PECVD. A strip-like pattern of 8 μm in width is formed on lower limiting layer 601 by photolithography. Then, an Au thin film 603 of 20 nm in thickness is formed by sputtering or vapor deposition, and a measurement Au arm 21, a first reference Au arm 22 and a second reference Au arm 23 are formed by lifting or wet etching. Thereafter a buffer layer 604 made of $SiO_x$ or $SiN_y$ is formed by a method such as sputtering, vapor deposition or spin coater hardening.

In response to specific measurement conditions, the thickness of buffer layer 604 is set to 10 nm to 1 μm. Upper limiting layer 602 is formed by PECVD. Finally, a measurement window 605 of 2 mm in length and 200 μm in width is formed by wet or dry etching. The aforementioned chip is fixed, and an incident optical fiber 91 and a sensing optical fiber 92 are fixed to both sides thereof. The heights of incident optical fiber 91 and sensing optical fiber 92 must be conformed to the center of first reference Au arm 22, and the length of first reference Au arm 22 between incident optical fiber 91 and sensing optical fiber 92 is 3 mm. A field of light from incident optical fiber 91 excites surface plasmon polaritons on first reference Au arm 22. The thickness of the Au thin film is appropriate, whereby upper and lower surface plasmon polaritons are coupled to form a long-range surface plasmon polariton transmittable in a constant distance. The transmitted surface plasmon polariton is sensed by sensing optical fiber 92, the position of the optical fiber is adjusted, and the position in the vertical direction thereof is fixed while the horizontal position is adjusted up to measurement Au arm 21 when an output reaches the maximum.

Figure 10:
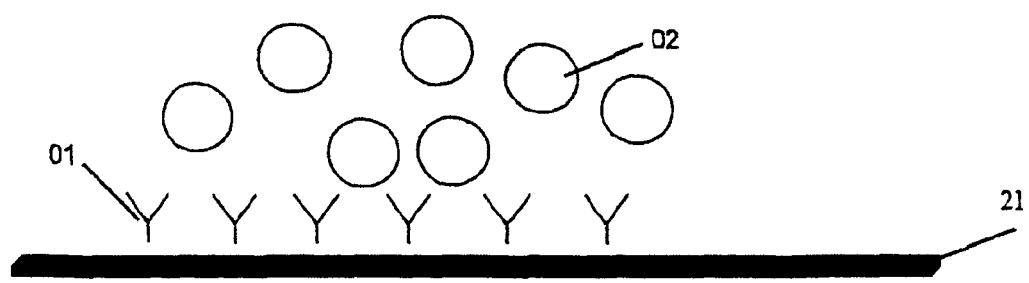
FIG. 10 is a diagram showing a sensing chip of a long-range surface plasmon polariton for a refractive index according to Example 2, including organic antibodies 01, organic antigens 02 and a measurement Au arm 21 therein.

The sensor surface is treated with a mixed liquid of sulfonic acid and hydrogen peroxide water. At this time, the apparatus is dipped in an ethanol solvent containing aminopropyl triethoxysilane. The apparatus is rinsed with water, ethanol and water respectively after this operation. The apparatus is reacted in a BS3 solution. At this time, anti-mouse Ig antibodies are fixed to the sensing surface. A fine passage pattern of PDMS is formed on the apparatus surface. Measurement is executed with a fine passage system. A mouse IgG solution is injected into the surface to which anti-IgGs are fixed. At this time, an output source changes in response to immune interaction. In other words, organic antibodies 01 (anti-mouse IgG antibodies) are formed and fixed in measurement window 605, and a liquid containing organic antigens 02 (IgGs) is introduced, as shown in FIG. 10. In this case, the refractive index in the measurement window changes with the antigen concentration. In this case, transmission loss of the long-range surface plasmon polariton can be sensitively changed unless the overall change in the refractive index of a dielectric in the measurement window exceeds a measurement range 8 shown in FIG. 4, the power of the surface plasmon polariton sensed by sensing optical fiber 92 changes by a change in the refractive index of a measurement-waiting substance, and hence the object of refractive index measurement can be attained. The change in the refractive index of the dielectric may result from reaction between substances, and there are also a change in the overall refractive index of the substance resulting from a temperature, a pressure, an electromagnetic field, luminous intensity or the like and a change in the whole of the refractive indices of the substance components resulting from external environment. This Example further introduces organic application in addition of the said Example, and further embodies the same than the said Example.

The material for the Au thin film in this Example may be replaced with any one of silver, aluminum, copper, titanium, nickel and chromium or an alloy thereof, and the material for the Si substrate may be replaced with a material such as $SiO_2$, GaAs, InP, Cu or Al. This exerts no influence on the service function of this Example.

Example 3

FIGS. 6, 7, 8 and 9 show the basic structure of Example 3 of a sensing chip for a refractive index of a long-range surface plasmon polariton. An Si substrate 10 is selected. BCB is selected as the material for a lower limiting layer 601 and an upper limiting layer 602, and lower limiting layer 601 is formed on Si substrate 10 by spin coater hardening. A strip-like pattern of 8 μm in width is formed on lower limiting layer 601 by photolithography. Then, an Au thin film 603 of 20 nm in thickness is formed by sputtering or vapor deposition, and a measurement Au arm 21, a first reference Au arm 22 and a second reference Au arm 23 are formed by lifting or wet etching. Thereafter a buffer layer 604 made of $SiO_x$ or $SiN_y$ is formed by a method such as sputtering, vapor deposition or spin coater hardening. In response to specific measurement conditions, the thickness of buffer layer 604 is set to 10 nm to 1 μm. Upper limiting layer 602 is formed by spin coater hardening. Finally, a measurement window 605 of 2 mm in length and 200 μm in width is formed by wet or dry etching. The aforementioned chip is fixed, and an incident optical fiber 91 and a sensing optical fiber 92 are fixed to both sides thereof. The heights of incident optical fiber 91 and sensing optical fiber 92 must be conformed to the center of first reference Au arm 22, and the length of first reference Au arm 22 between incident optical fiber 91 and sensing optical fiber 92 is 3 mm. A light field emitted from incident optical fiber 91 excites surface plasmon polaritons on first reference Au arm 22. The thickness of the Au thin film is appropriate, whereby upper and lower surface plasmon polaritons are coupled to form a long-range surface plasmon polariton transmittable in a constant distance. The transmitted surface plasmon polariton is sensed by sensing optical fiber 92, the position of the optical fiber is adjusted, and the position in the vertical direction thereof is fixed while the horizontal position is adjusted up to measurement Au arm 21 when an output reaches the maximum. In this case, a measurement-waiting substance (transparent liquid whose refractive index is not larger than that of BCB) is introduced into measurement window 605. Transmission loss of the long-range surface plasmon polariton can be sensitively changed unless the overall change in the refractive index of a dielectric in the measurement window exceeds a measurement range 8 shown in FIG. 4, the power of the surface plasmon polariton sensed by sensing optical fiber 92 changes by the change in the refractive index of the measurement-waiting substance, and hence the object of refractive index measurement can be attained. The change in the refractive index of the dielectric may result from reaction between substances, and there are also a change in the overall refractive index of the substance resulting from a temperature, a pressure, an electromagnetic field, luminous intensity or the like and a change in the whole of the refractive indices of the substance components resulting from external environment. In this Example, the refractive index of BCB resin is higher and becomes about 1.53, limitation with respect to the long-range surface plasmon polariton is stronger, the long-range surface plasmon polariton is further sensitive to a surface change, and some requests for specific application can be satisfied. Further, the process of BCB is simpler, and suitable to an experiment and manufacturing.

The material for the Au thin film in this Example may be replaced with any one of silver, aluminum, copper, titanium, nickel and chromium or an alloy thereof, and the material for the Si substrate may be replaced with a material such as $SiO_2$, GaAs, InP, Cu or Al. This exerts no influence on the service function of this Example.

Example 4

FIGS. 6, 7, 8 and 9 show the basic structure of Example 4 of a sensing chip for a refractive index of a long-range surface plasmon polariton. An Si substrate 10 is selected. $SiO_2$ or $SiO_x$ is selected as the material for a lower limiting layer 601 and an upper limiting layer 602, and lower limiting layer 601 is formed on Si substrate 10 by spin coater hardening. A strip-like pattern of 8 μm in width is formed on lower limiting layer 601 by photolithography. Then, an Au thin film 603 of 20 nm in thickness is formed by sputtering or vapor deposition, and a measurement Au arm 21, a first reference Au arm 22 and a second reference Au arm 23 are formed by lifting or wet etching. Thereafter a buffer layer 604 made of $SiO_x$ or $SiN_y$ is formed by a method such as sputtering, vapor deposition or spin coater hardening. In response to specific measurement conditions, the thickness of buffer layer 604 is set to 10 nm to 1 μm. Upper limiting layer 602 is formed by PECVD. Finally, a measurement window 605 of 2 mm in length and 200 μm in width is formed by wet or dry etching. The aforementioned chip is fixed, and an incident optical fiber 91 and a sensing CCD 92 are fixed to both sides thereof. The heights of incident optical fiber 91 and sensing CCD 92 must be conformed to the center of first reference Au arm 22, and the length of first reference Au arm 22 between incident optical fiber 91 and sensing CCD 92 is 3 mm. A light field emitted from incident optical fiber 91 excites surface plasmon polaritons on first reference Au arm 22. The thickness of the Au thin film is appropriate, whereby upper and lower surface plasmon polaritons are coupled to form a long-range surface plasmon polariton transmittable in a constant distance. The transmitted surface plasmon polariton is sensed by sensing CCD 92, the position of the optical fiber is adjusted, and the position in the vertical direction thereof is fixed while the horizontal position is adjusted up to measurement Au arm 21 when an output reaches the maximum. In this case, a measurement-waiting substance (transparent liquid whose refractive index is smaller than that of $SiO_2$) is introduced into measurement window 605. Transmission loss of the long-range surface plasmon polariton can be sensitively changed unless the overall change in the refractive index of a dielectric in the measurement window exceeds a measurement range 8 shown in FIG. 4, and a light spot size (and power) of the surface plasmon polariton sensed by sensing CCD 92 changes by the change in the refractive index of the measurement-waiting substance. As compared with Example 1, the change in the light spot size resulting from the refractive index is measured through the CCD, whereby higher precision can be obtained.

The material for the Au thin film in this Example may be replaced with any one of silver, aluminum, copper, titanium, nickel and chromium or an alloy thereof, and the material for the Si substrate may be replaced with a material such as $SiO_2$, GaAs, InP, Cu or Al. This exerts no influence on the service function of this Example.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A sensing chip for measuring a refractive index of a long-range surface plasmon polariton, having a thin metal film or a strip-like metal as well as an upper limiting layer and a lower limiting layer made of silicon-rich silica $SiO_x$ (where $0<x<2$), $SiO_2$ or benzocyclobutene (BCB) and a dielectric buffer layer formed on the upper and lower surfaces thereof, wherein said dielectric buffer layer is made of silicon-rich silica $SiO_x$ (where $0<x<2$) or silicon nitride $SiN_y$ (where $0<y<4/3$), and attached onto a measurement groove of the metal thin film or the strip-like metal, the metal thin film or the strip-like metal and the buffer layer are sandwiched between said upper limiting layer and said lower limiting layer, and the upper layer surface of said upper limiting layer made of $SiO_x$, $SiO_2$ or benzocyclobutene is perforated to form the measurement groove, all of the aforementioned structures are grown on an Si underlayer, a GaAs underlayer, an InP underlayer or an $SiO_2$ underlayer, and the sensing chip is arranged so that the refractive index of a long-range surface plasmon polariton is measured by forming a long-range surface plasmon polariton by performing excitation on an end face of said metal thin film or said strip-like metal, and measuring a refractive index change of a liquid in the measurement groove or an antigen-antibody reaction of an organism from a change in transmission loss of said long-range surface plasmon polariton and/or a change in a light spot size.

2. The sensing chip according to claim 1, wherein the metal in said metal thin film or said strip-like metal is any one of gold, silver, aluminum, copper, titanium, nickel and chromium, the thickness of the metal thin film is 1 nm to 100 nm, and the width of the strip-like metal is 50 nm to 100 μm.

3. The sensing chip according to claim 1, wherein said upper limiting layer and said lower limiting layer are dielectrics, the refractive indices thereof are 1.0 to 4.0, and the thicknesses of these dielectrics are 1 to 10000 nm.

4. The sensing chip according to claim 1, wherein said dielectric buffer layer is made of $SiO_x$ (where $0<x<2$) or $SiN_y$ (where $0<y<4/3$), the refractive index thereof is 1.0 to 4.0, and the thickness of this dielectric is 1 to 10000 nm.

5. The sensing chip according to claim 1, wherein the thickness of said upper limiting layer or said lower limiting layer made of $SiO_2$ is 1 μm, and the thickness of said upper limiting layer or said lower limiting layer made of benzocyclobutene is larger than 1 μm.

6. The sensing chip according to claim 1, wherein a bio material is fixed onto the dielectric buffer layer in the measurement groove.

* * * * *